United States Patent
Navarro-Paredes et al.

(10) Patent No.: US 9,238,146 B2
(45) Date of Patent: Jan. 19, 2016

(54) EXTERNAL DEFIBRILLATOR

(71) Applicant: Heartsine Technologies Limited, Belfast (GB)

(72) Inventors: Cesar Oswaldo Navarro-Paredes, Newtownabbey (GB); John McCune Anderson, Hollywood Down (GB); Janice Anderson, Hollywood Down (GB)

(73) Assignee: Heartsine Technologies Limited, Belfast (GB)

( * ) Notice: Subject to any disclaimer, the term of this patent is extended or adjusted under 35 U.S.C. 154(b) by 0 days.

(21) Appl. No.: 14/561,571

(22) Filed: Dec. 5, 2014

(65) Prior Publication Data

US 2015/0088215 A1 Mar. 26, 2015

Related U.S. Application Data

(63) Continuation of application No. 13/990,059, filed as application No. PCT/EP2011/071069 on Nov. 25, 2011, now Pat. No. 8,909,336.

(30) Foreign Application Priority Data

Nov. 29, 2010 (IE) .................................. S2010/0746

(51) Int. Cl.
*A61N 1/00* (2006.01)
*A61N 1/39* (2006.01)
*A61B 5/0452* (2006.01)
*A61B 5/053* (2006.01)
*A61B 5/00* (2006.01)

(52) U.S. Cl.
CPC ............ *A61N 1/3918* (2013.01); *A61B 5/0452* (2013.01); *A61B 5/0535* (2013.01); *A61B 5/721* (2013.01); *A61B 5/7207* (2013.01); *A61B 5/7239* (2013.01); *A61N 1/3925* (2013.01); *A61N 1/3931* (2013.01); *A61N 1/3987* (2013.01)

(58) Field of Classification Search
CPC ... A61N 1/3918; A61N 1/3987; A61N 1/365; A61N 1/39; A61B 5/02
See application file for complete search history.

(56) References Cited

U.S. PATENT DOCUMENTS

| 4,619,265 A | 10/1986 | Morgan et al. |
| 5,247,939 A | 9/1993 | Sjoquist et al. |
| 6,287,328 B1 | 9/2001 | Snyder et al. |

(Continued)

FOREIGN PATENT DOCUMENTS

| EP | 2 172 245 A1 | 4/2010 |
| WO | WO 2009/109595 A1 | 9/2009 |

*Primary Examiner* — Robert N Wieland
(74) *Attorney, Agent, or Firm* — Novak Druce Connolly Bove + Quigg LLP

(57) ABSTRACT

An external defibrillator includes patient electrodes (20) for obtaining the patient's electrocardiogram (ECG) and for applying a shock to the patient. A microprocessor (24) analyses the patient's ECU using a diagnostic algorithm to detect if the patient's heart is in a shockable rhythm, and shock delivery circuitry (10) is enabled when a shockable rhythm is detected by the diagnostic algorithm. The patient electrodes also allow obtaining a signal (Z) which is a measure of the patient's transthoracic impedance and the microprocessor is responsive to Z to detect conditions likely to cause the diagnostic algorithm to generate a false detection of a shockable rhythm. If such detection is made, the microprocessor prevents detection of a shockable rhythm by the diagnostic algorithm, at least for a period of time.

18 Claims, 3 Drawing Sheets

(56) References Cited

U.S. PATENT DOCUMENTS

2006/0025825 A1 2/2006 Bowers
2011/0224746 A1 9/2011 Didon
2012/0035676 A1* 2/2012 Owen et al. .................. 607/6
2012/0302896 A1 11/2012 Joo et al.

* cited by examiner

EXTERNAL DEFIBRILLATOR

CROSS REFERENCE TO RELATED APPLICATIONS

This is a continuation of U.S. application Ser. No. 13/990,059, filed May 29, 2013, now patented as U.S. Pat. No. 8,909,336, which is a national stage application under 35 U.S.C. §371 of International Application No. PCT/EP2011/071069, filed Nov. 25, 2011, and claims the benefit of European Application No. S2010/0746, filed Nov. 29, 2010, the disclosures of all of which are incorporated herein by reference.

This invention relates to an external defibrillator.

External automated defibrillators are normally connected to a patient via two electrodes. An electrocardiogram (ECG) and the patient's transthoracic impedance (ICG) are continuously recorded by the defibrillator and analysed using a diagnostic algorithm in order to detect a shockable rhythm, e.g. ventricular fibrillation (VF). If such a rhythm is found, the defibrillator prompts an audible/visible message to the operator (rescuer) to activate the defibrillator to deliver a therapeutic shock which may allow the patient to regain a perfused rhythm.

The use of a defibrillator involves a stressful time for the operator where the patient requires a fast and adequate treatment. The patient could be moved during preparation for CPR or checking for vital signs, etc., or the electrodes could be inadvertently touched after their application to the patient and while the ECG is being analysed. Any of these actions can introduce noise into the ECG and ICG signals being acquired by the defibrillator through the attached electrodes. This signal noise can mislead the diagnostic algorithm and cause it to generate a false determination of a shockable rhythm. This represents a risk to the patient when a non-shockable rhythm is wrongly classified as a shockable one and a risk to the operator when a shock is delivered while manipulating the patient.

It is therefore desirable that lay responders using public access defibrillators are provided with more reliable and safer devices.

According to an aspect of the present invention, there is provided an external defibrillator as specified in claim 1.

According to the invention there is provided an external defibrillator including patient electrodes for obtaining the patient's electrocardiogram (ECG) and for applying a shock to a patient, circuit means for analysing the patient's ECG using a diagnostic algorithm to detect if the patient's heart is in a shockable rhythm, and shock delivery circuitry which is enabled when a shockable rhythm is detected by the diagnostic algorithm, wherein the patient electrodes also allow obtaining a signal (Z) which is a measure of the patient's transthoracic impedance and the circuit means is responsive to Z to detect interference conditions likely to cause the diagnostic algorithm to generate a false detection of a shockable rhythm and, if such detection is made, to prevent detection of a shockable rhythm by the diagnostic algorithm, at least for a period of time.

In a preferred embodiment the circuit means detects said conditions by forming the first derivative dZ/dt of Z, deriving a quantity related to the energy of dZ/dt in a moving time window, and determining if said energy-related quantity exceeds a certain threshold level.

The present invention uses the patient's transthoracic impedance to detect when a faulty classification is likely to occur, since the impedance signal is more sensitive to interferences such as movement of the patient and touching electrodes by the operator than the ECG. Dramatic changes observed in the patient's impedance are strong indicators of interferences such as those mentioned above taking place.

An embodiment of the invention will now be described, by way of example, with reference to the accompanying drawings, in which.

Figure 1:
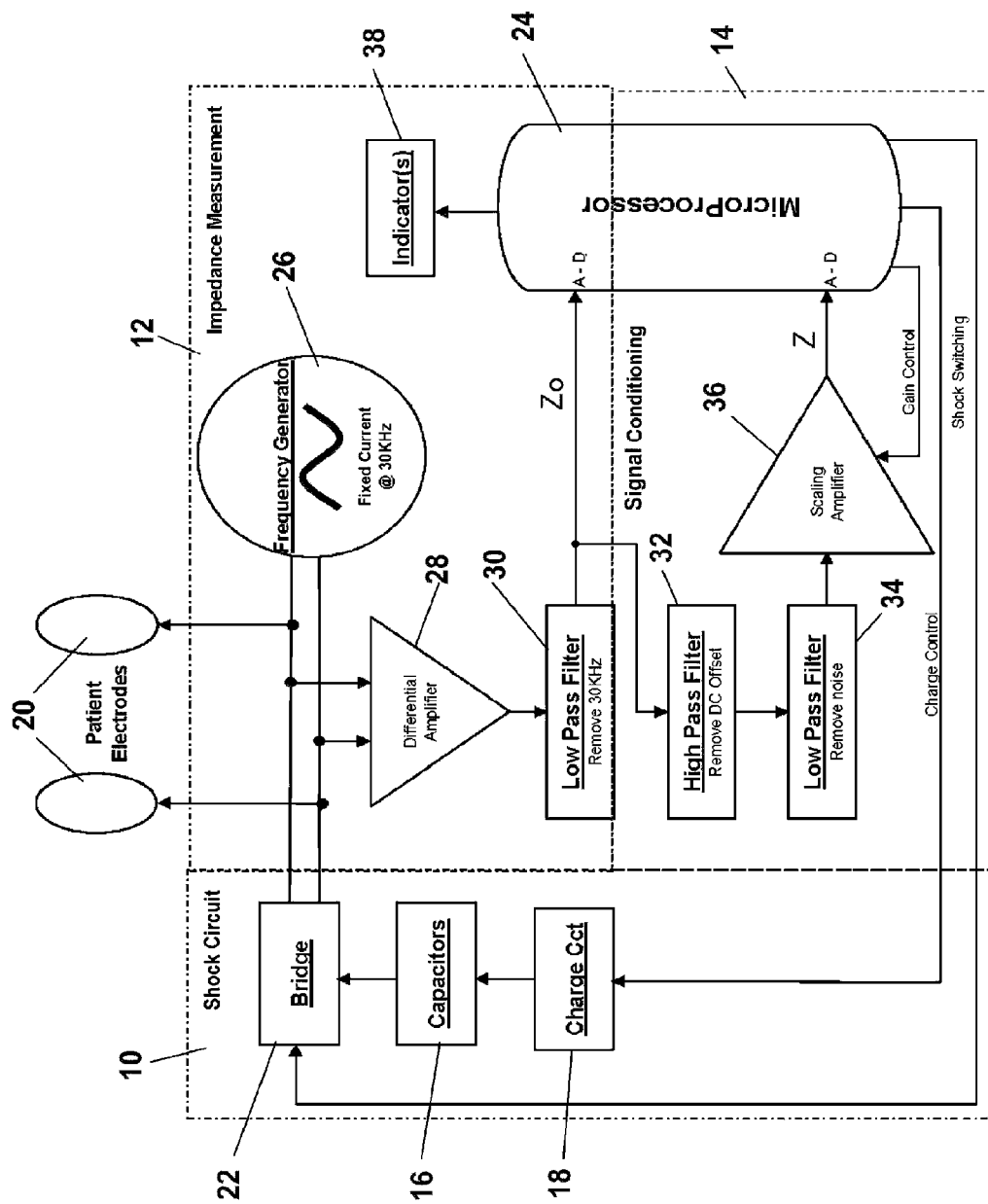
FIG. 1 is a block diagram of an automated external defibrillator embodying the invention.

Referring to FIG. 1, an automated external defibrillator comprises three main sections: 10, 12 and 14.

Section 10 is the main high voltage shock circuitry and comprises a bank of capacitors 16 which are charged up to a high voltage by a charging circuit 18, the charge being released as a bi-phasic high voltage shock through a pair of patient electrodes 20 by a bridge circuit 22. The charging of the capacitors 16 and the shape and duration of the bi-phasic shock waveform is controlled by a microprocessor 24, the actual shock being given by the user pressing a button (not shown) if the patient's condition is deemed "shockable" as determined by a diagnostic algorithm having the patient's ECG as input. The ECG is derived from the patient electrodes 20 in known manner, not shown. The process is prompted by voice messages and/or visual prompts output on visual/audio indicators 38 (the indicators are shown in section 12 for diagrammatic simplicity). The audio/visual output indicators 38 may comprise a loudspeaker and/or LED(s).

Section 12 measures the patient's transthoracic impedance using the same electrodes 20 as are used for applying the shock. A generator 26 produces a 30 kilohertz sinusoidal waveform at a constant current of 100 microamperes. This signal is applied across the electrodes 20. When the electrodes are attached to a patient, a voltage across the electrodes is generated which is superimposed on the 30 kHz sinusoid. This voltage is a direct measurement of the transthoracic impedance of the patient. The voltage generated in response to the sinusoid is applied to a differential amplifier 28 which converts it from a differential signal to a single signal referenced to ground potential. The resultant waveform is passed through a low pass filter 30 which removes the original 30 kHz signal leaving a signal Zo (static impedance) which is directly proportional to the patient impedance. The impedance signal Zo is used by the microprocessor 24 to set the bi-phasic pulse amplitude and width to ensure that the correct total energy (typically 150 Joules) is delivered to the patient.

The construction and operation of sections 10 and 12 of the AED are well-known, and it is not thought that further detail is necessary.

The purpose of section 14 is to provide further conditioning of the impedance signal Zo as input to an algorithm to detect circumstances likely to cause the main diagnostic algorithm to generate a false detection of a shockable rhythm. Section 14 is additional to the existing circuitry for the derivation of patient impedance in section 12.

In section 14 of the defibrillator the impedance signal Zo which is output from the low pass filter 30 is passed through a high pass filter 32 which removes the dc offset before removing higher frequency noise in the low pass filter 34. Finally the signal is scaled in an amplifier 36 incorporating digital gain control to a level appropriate for analogue-to-digital conversion by the microprocessor 24. The resultant filtered and amplified signal Z is digitally converted. In this embodiment the analog to digital sample rate is 170.66 samples per second. However, this is not a limitation for the detection of interference since adjustments in thresholds are possible to adapt to a different sample rate. The impedance signal Z is differentiated and the result dZ/dt is used in an algorithm, FIG. 3, to detect interference conditions likely to cause the diagnostic algorithm to cause it to generate a false detection of a shockable rhythm.

Figure 2:
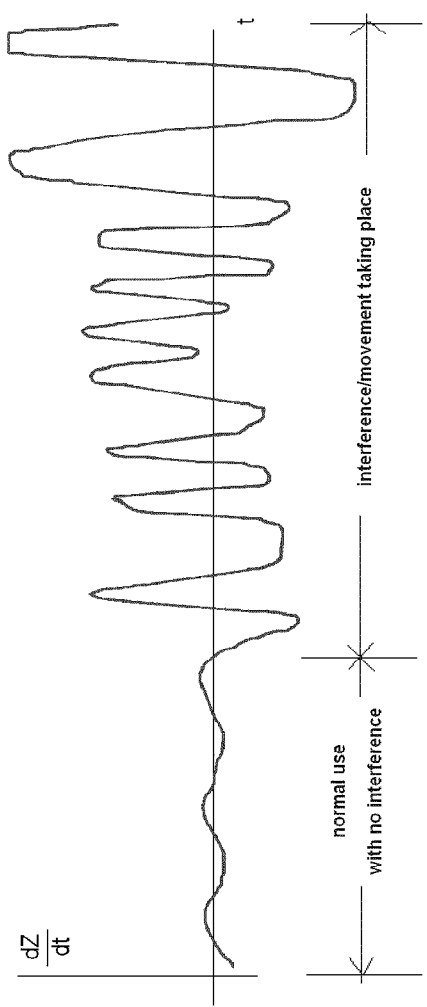
FIG. 2 is an impedance waveform illustrating the first derivative dZ/dt of the impedance signal Z during periods of no interference and interference respectively.
Figure 3:
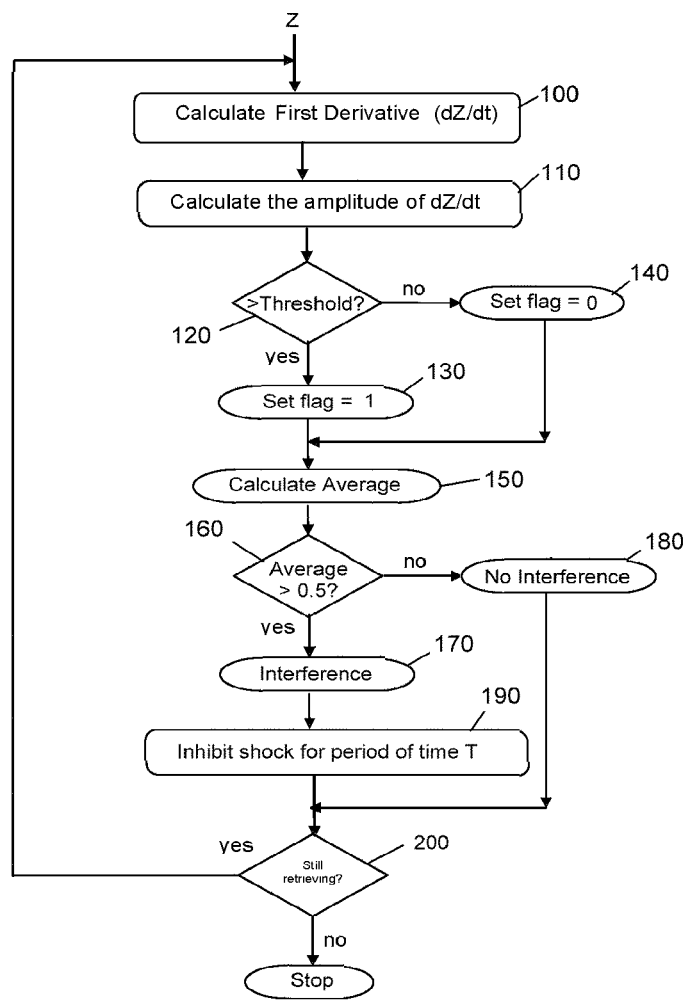
FIG. 3 is a flow diagram of an algorithm to detect conditions likely to cause the diagnostic algorithm to generate a false detection of a shockable rhythm.

First, however, reference is made to FIG. 2 which shows a typical dZ/dt waveform during periods of no interference and interference respectively. On the left the signal has a relatively low energy, corresponding to a period when the patient and the electrodes are undisturbed. On the right, however, the signal becomes relatively much more energetic, corresponding to a period when the patient and/or electrodes are disturbed sufficiently to cause, or be likely to cause, the diagnostic algorithm to generate a false detection of a shockable rhythm. The algorithm of FIG. 3 is therefore designed to detect periods when the energy of dZ/dt is above a threshold level likely to cause false detection. In particular, in the preferred embodiment, the algorithm detects disturbances likely to cause the diagnostic algorithm to generate a false detection of a shockable rhythm by forming the first derivative of Z (dZ/dt), deriving a signal related to the energy of dZ/dt in a moving time window, and determining if the energy signal exceeds a certain (empirically determined) threshold level.

Referring now to FIG. 3, in respect of successive (preferably consecutive) digital values of Z input to the microprocessor 24 from the scaling amplifier 36 the algorithm performs the following steps for each such value:

a. At step 100 the signal Z is differentiated by software in the microprocessor 24 to obtain its first derivative dZ/dt.
b. Next, step 110, the amplitude of dZ/dt is calculated.
c. Next, step 120, if the amplitude of the signal dZ/dt is greater than a certain threshold a flag is set to 1, step 130, otherwise the flag is set to 0, step 140.
d. The flag values (0 or 1) are averaged over the last 0.75 s, step 150. This is done by feeding a binary array of 128 elements (equivalent to 0.75 s using a 170.66 sample rate). The oldest value in the array is substituted by the newest one, and the elements of the binary array are summed and divided by 128.
e. If this average is greater than 0.5, step 160, which means that most of the time dZ/dt has been higher than the threshold, the algorithm flags that it has detected interference or disturbance likely to cause the diagnostic algorithm to generate a false detection of a shockable rhythm (step 170). Otherwise no interference or disturbance is detected, step 180.
f. In the case of interference being found at step 170 the diagnostic algorithm in the defibrillator is prevented from detecting a shockable rhythm for a period of, in this embodiment, 4 seconds (step 190).

The process continues (step 200) until no more Z values are input, i.e. the Z signal is no longer present.

The threshold value used in step 120 of this embodiment was obtained empirically by analysing a large volume of patient data when interferences was documented. Additionally, the threshold value depends on the A-D sample rate, the gain from the amplifier 36, the resolution of Z, the length of the moving time window, the technique used for calculating dZ/dt, etc.

It will be evident that in this embodiment the average calculated at step 150 is a measure of the energy of the dZ/dt signal over the preceding 0.75 s window. That is to say, the more often the amplitude of dZ/dt exceeds the threshold in the moving window, the greater the energy of the signal.

However, other methods of measuring the energy of the signal in a moving time window can be used in other embodiments of the invention. For example, the RMS value of the signal can be calculated, or peak-to-peak value.

The invention is not limited to the embodiment described herein which may be modified or varied without departing from the scope of the invention.

The invention claimed is:

1. A defibrillator comprising:
   electrodes;
   a processor; and
   a circuit connecting the processor and the electrodes, wherein, when the electrodes are in contact with a patient, the processor performs operations comprising:
      receiving a signal from the patient;
      determining, from the signal, a measure of transthoracic impedance of the patient;
      identifying, based on the measure of transthoracic impedance, that an interference condition is present, wherein the interference condition causes a false detection of a shockable rhythm in the patient; and
      performing, based on the interference condition, one of:
         inhibiting the circuit from delivering a shock to the patient and preventing a diagnostic algorithm from detecting a shockable rhythm.

2. The defibrillator of claim 1, wherein the interference condition is one of a movement of the patient and a touching of the electrodes by an operator.

3. The defibrillator of claim 1, wherein when the electrodes are in contact with a patient, the processor performs further operations comprising:
   establishing an electrocardiogram of the patient.

4. The defibrillator of claim 3, wherein inhibiting the circuit from delivering a shock to the patient is independent of the electrocardiogram.

5. The defibrillator of claim 1, wherein inhibiting the circuit from delivering a shock to the patient is performed for a predefined period of time.

6. The defibrillator of claim 1, wherein when the electrodes are in contact with a patient, the processor performs further operations comprising:
   identifying that the interference condition is present by forming a first derivative of the measure of transthoracic impedance with respect to a period of time to yield a first derivative; and
   deriving a quantity of interference related to the first derivative.

7. The defibrillator of claim 6, wherein when the electrodes are in contact with a patient, the processor performs further operations comprising:
   determining if the quantity of interference exceeds a threshold level.

8. The defibrillator of claim 7, wherein the quantity of interference is a measure of the number of times the amplitude of the first derivative exceeds the threshold level.

9. The defibrillator of claim 1, wherein when the electrodes are in contact with the patient, the processor performs additional operations comprising:
   converting the measure of transthoracic impedance from analog to digital, to yield a digital signal; and
   using the digital signal for the identifying that the interference condition is present.

10. A method comprising:
   receiving a signal from a patient via electrodes;
   determining, from the signal and via a processor, a measure of transthoracic impedance of the patient;

identifying, based on the measure of transthoracic impedance, that an interference condition is present, wherein the interference condition causes a false detection of a shockable rhythm in the patient; and performing, based on the interference condition, one of: inhibiting the circuit from delivering a shock to the patient and preventing a diagnostic algorithm from detecting a shockable rhythm.

11. The method of claim 10, wherein the interference condition is one of a movement of the patient and a touching of the electrodes by an operator.

12. The method of claim 11, further comprising:
establishing an electrocardiogram of the patient.

13. The method of claim 12, wherein inhibiting the circuit from delivering a shock to the patient is independent of the electrocardiogram.

14. The method of claim 11, wherein inhibiting the circuit from delivering a shock to the patient is performed for a predefined period of time.

15. The method of claim 11, further comprising:
determining when the interference condition is present by forming a first derivative of the measure of transthoracic impedance with respect to a period of time to yield a first derivative; and
deriving a quantity of interference related to the first derivative.

16. The method of claim 15, further comprising:
determining if the quantity of interference exceeds a threshold level.

17. The method of claim 16, wherein the quantity of interference is a measure of the number of times the amplitude of the first derivative exceeds the threshold level.

18. The method of claim 11, further comprising:
converting the measure of transthoracic impedance from analog to digital, to yield a digital signal; and
using the digital signal for the identifying that the interference condition is present.

* * * * *